(12) United States Patent
Hahn et al.

(10) Patent No.: US 6,269,686 B1
(45) Date of Patent: Aug. 7, 2001

(54) SENSOR, IN PARTICULAR FOR MEASURING THE VISCOSITY AND DENSITY OF A MEDIUM

(75) Inventors: Dietmar Hahn, Gerlingen; Gottfried Flik; Falk Herrmann, both of Leonberg, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/244,594

(22) Filed: Feb. 4, 1999

(30) Foreign Application Priority Data

Feb. 4, 1998 (DE) .............................................. 198 04 326

(51) Int. Cl.[7] .............................. G01N 11/10; G01N 9/36; G01N 9/00
(52) U.S. Cl. ........................ 73/54.24; 73/24.05; 73/32 A
(58) Field of Search ................................. 73/54.14, 54.24, 73/54.25, 54.26, 54.32, 54.34, 54.41, 73, 24.05, 30.01, 32 R, 32 A

(56) References Cited

U.S. PATENT DOCUMENTS

| 3,734,119 | * | 5/1973 | Nudds | 137/92 |
| 4,799,378 | * | 1/1989 | Portman, Jr. et al. | 73/54.27 |
| 5,067,344 | * | 11/1991 | Fitzgerald et al. | 73/54.24 |
| 5,201,215 | * | 4/1993 | Granstaff et al. | 73/54.41 |
| 5,571,952 | * | 11/1996 | Kauzlarich | 73/54.24 |

FOREIGN PATENT DOCUMENTS

| 03202748 | * | 9/1991 | (JP) | G01N/11/16 |
| 3202748 | * | 9/1991 | (JP) | G01N/11/16 |

* cited by examiner

Primary Examiner—Hezron Williams
Assistant Examiner—Jay L. Politzer
(74) Attorney, Agent, or Firm—Kenyon & Kenyon

(57) ABSTRACT

A sensor which has a bending reed and a piezoelectric resonator. Due to excitation by the piezoelectric resonator, the bending reed can be excited to vibration in a measurable medium. In this context, the vibration frequency and the damping of the bending reed are a function of the density and the viscosity, respectively, of the measurable medium. This can be measured by a piezoresistive element, and thus the density and viscosity of the measurable medium are ascertained.

8 Claims, 1 Drawing Sheet

SENSOR, IN PARTICULAR FOR MEASURING THE VISCOSITY AND DENSITY OF A MEDIUM

FIELD OF THE INVENTION

The present invention is directed to a sensor, in particular for measuring the density and viscosity of a medium.

BACKGROUND INFORMATION

A known sensor for measuring the density and viscosity of liquids is described in the article by Inaba et al, Sensors and Actuators A, 33 (1991), pages 163–166. In this known sensor, a bending reed is dipped into the medium, and is excited to a thermally induced vibration by irradiation with the assistance of a laser diode. The vibrational frequency is influenced by the density of the medium, and the damping of the vibration is influenced by the viscosity of the medium. Thus, the density and viscosity of the medium, which may correspond to a liquid, can be measured by measuring the vibration of the bending reed.

SUMMARY OF THE INVENTION

In contrast, the sensor of the present invention has the advantage that a particularly simple and trouble-free design is utilized. In particular, since the sensor of the present invention can be constructed to be especially small, the sensor of the present invention is also suitable for checking very small liquid or gas quantities.

By using silicon nitride, silicon oxide, metal, or mixed materials of the aforesaid, a bending reed used in the present invention is produced which is resistant to most chemical media. Therefore, such a sensor can be used for a multitude of measurable media. Furthermore, because these materials can be processed in few and well-controlled standard processes, cost-effective production in large lots is made possible. Moreover, such bending reeds can be made particularly small. Since the vibration generator is arranged on the facing-away side of a silicon substrate, the measurable medium only comes in contact with very chemically-resistant materials. Thus, vibration generators can also be used which are not so chemically resistant. The vibrations of the bending reed are detected particularly simply by a monocrystalline piezoresistive element. Such an element is also resistant to most chemical media. Alternatively, a piezoresistive thin film can also be used on the top side of the bending reed. In addition, the temperature of the measurable medium can also be ascertained by a temperature sensor on the substrate. The measured temperature can also be taken into account in calculating the density and viscosity of the measurable medium. A signal-processing circuit is advantageously integrated directly on the silicon substrate, since in this way, particularly good signal processing is achieved. The influence of parasitic variables is reduced, and the evaluating electronics can thus be more compactly, and generally also more cost-effectively produced. By appropriate feedbacks, both vibrations of maximum amplitude and of maximum speed can be attained in the zero passage.

DETAILED DESCRIPTION

Figure 1:
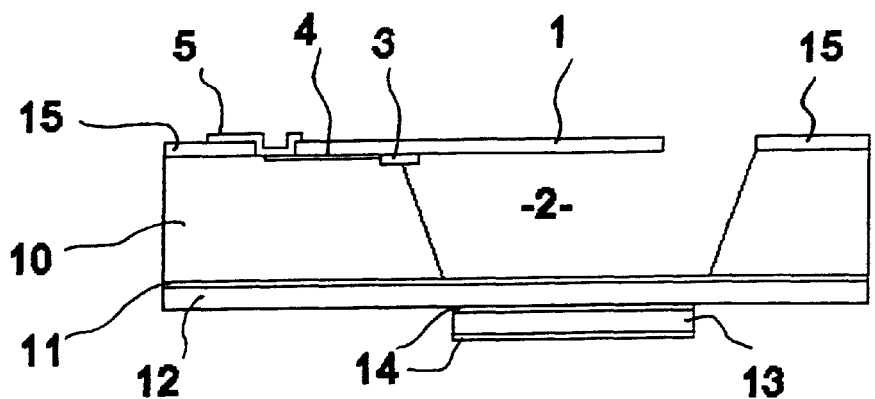
FIG. 1 shows a cross-section of a first exemplary embodiment according to the present invention.

FIG. 1 shows a cross-section of a sensor according to a first embodiment of the present invention. The sensor has a substrate 10 formed of silicon, upon whose top side a bending reed 1 is arranged. Underneath bending reed 1, a groove well 2 is introduced into substrate 10, so that bending reed 1 can vibrate freely in a direction normal to the top surface of substrate 10. Besides silicon, other materials may serve as substrate 10, into which corresponding recesses are introduced. In the region where bending reed 1 rests on substrate 10, a piezoresistive resistor element 3 is configured underneath bending reed 1. This piezoresistive resistor element 3 is appropriately doped silicon which, because of mechanical stresses, changes its electrical resistance (p)iezoresistive effect). Piezoresistive resistor element 3 is connected to a metallic contacting 5 by a printed circuit trace 4 which is likewise diffused into substrate 10. Bending reed 1 is patterned out of a silicon nitride layer 15 applied on the top side of substrate 10. On the bottom side, substrate 10 has an etching stop layer 11, which also forms the bottom of groove well 2. Etching stop layer 11 is made, e.g., of silicon oxide, silicon nitride, highly doped silicon, or another material which can be used particularly well as an etching stop layer when groove well 2 is etched. Underneath etching stop layer 11, provision is also made for an acoustic coupling layer 12 which can be made, e.g., of glass (such as Pyrex glass) or plastic layers such as PMMA (polymethyl methacrylate). A piezoelectric resonator 13, having in each case a metallization 14 on the top and bottom side, is then arranged on coupling layer 12. Suitable for such piezoelectric resonators are, for example, thin-film transducers made of zinc oxide or lead zirconate titanate, or integrated transducers made of PVDF (polyvinylidenefluoride) or piezoceramic materials. Bending reed 1 typically has a thickness of several micrometers (0.5 to several 10 micrometers) and lengths between 50 micrometers and 2000 micrometers. Typical widths of the bending reed 1 lie in the order of magnitude of several 10 to several 1000 micrometers. Layer film thicknesses of below one micrometer are generally used for etching stop layer 11. Layer film thicknesses between 10 and 200 micrometers are suitable for coupling layer 12.

The sensor shown in FIG. 1 is suitable for ascertaining the density and viscosity of media. To that end, the top side of substrate 10, and thus bending reed 1 as well, receives the medium to be measured, so that bending reed 1 is completely surrounded by the medium. Piezoelectric resonator 13 is excited to vibration by electrical excitation. These vibrations are transferred by mechanical coupling to bending reed 1. This can be effected both by solidmatter vibrations, and via the medium itself. Thus, by suitable selection of the excitation of piezoelectric resonator 13, bending reed 1 can be excited to vibration. For example, an appropriately suitable excitation of piezoelectric resonator 13 can be composed of a sequence of high-frequency vibration pulses of piezoelectric resonator 13, whose repetition rate is near a natural frequency of bending reed 1. Alternatively, it is possible to use single pulses, or else to excite piezoelectric resonator 13 with a frequency which corresponds to a natural frequency of bending reed 1. The result of this is that bending reed 1 vibrates in the medium surrounding it. This vibration of bending reed 1 can be measured by piezoresistive resistor element 3, since mechanical states of stress are produced in piezoresistive resistor element 3 as a function of the deflection of bending reed 1. Thus, these lead to a changed resistance of resistor element 3, and can be measured with the assistance of leads 4 under contactings 5.

Density and viscosity can be ascertained by evaluating the vibration of bending reed 1 in the medium. A first possibility lies in the speed resonance, i.e. bending reed 1 is driven by a feedback loop at a frequency at which the speed is maximized in the reversal point. In close approximation, this frequency is only a function of the medium density; the width of the resonance curve then supplies the viscosity. However, these methods can only be used under certain conditions. Due to the vibration of bending reed 1, a wave forms in the medium, whose wavelength results from the frequency of bending reed 1 and the speed of propagation in the medium. The wavelength should be perceptibly larger than the geometric dimensions of bending reed 1; the larger the wavelength is, the less is the residual influence of the viscosity on the speed resonance frequency. This condition is generally met by very small bending reeds. A further or additional possibility is offered by the amplitude resonance at which the amplitude of the vibration is maximized by the feedback. The amplitude resonance frequency is a function of the density and the viscosity, the width of the resonance curve is a function of the viscosity. By performing a subtraction operation using the measured value of the amplitude resonance frequency with the density (derived from the speed resonance frequency) or of the viscosity (derived from the width of the amplitude resonance curve), the other measured value can then be determined in each case. A further possibility is the observation of the free vibration of bending reed 1 after a pulse-like excitation, during which viscosity and density can then be calculated by a least-square-fit.

Figure 2:
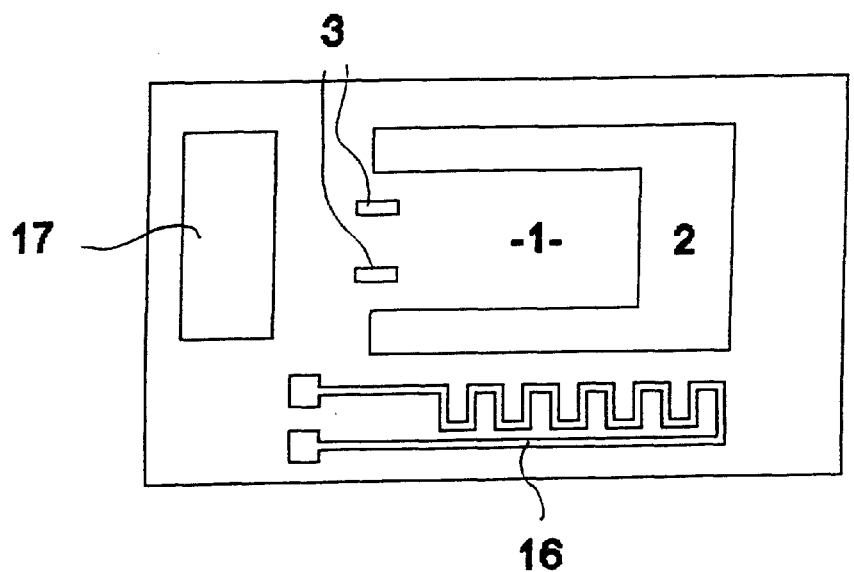
FIG. 2 show a top view of the first exemplary embodiment according to the present invention.

FIG. 2 shows a top view of the sensor according to FIG. 1, contactings 5 and traces 4 not being shown, to simplify the representation. In the top view, one can discern bending reed 1 and groove well 2 which surrounds bending reed 1. By way of example, also shown in the top view according to FIG. 2 are two piezoresistive resistor elements 3 which are arranged in the hanging region of bending reed 1. Such pluralities of piezoresistive resistor elements 3 can advantageously be interconnected to form half bridges or full bridges, thus simplifying the evaluation of the signals. Furthermore, a platinum resistor element 16 is also shown, which is arranged on the top side of nitride layer 15. Such a platinum resistor element 16 can be used for measuring the temperature of the medium, since both viscosity and density of a medium (both in the case of liquids and in the case of gases) are dependent upon this temperature. Therefore, such a temperature measurement can be drawn upon to calculate the influence of temperature on density and viscosity. Moreover, the temperature dependence of the mechanical constant of bending reed 1, and therefore the effect on the resonance frequency, is taken into account. The circuits necessary for that purpose can also be configured in substrate 10 itself. Such circuits were indicated by way of example in FIG. 2 by block 17. In addition to the use of a plurality of piezoresistive resistor elements 3, provision can also be made for a plurality of bending reeds 1 which have different dimensions. They can therefore be excited by different vibrational frequencies, which means a very large measuring range can be covered in particular during a viscosity measurement.

The use of a bending reed 1 made exclusively of silicon nitride is especially advantageous, since it is a particularly chemically-resistant material. Thermal strains of bending reed 1 are avoided by forming it from a single material. Alternatively, bending reed 1 can also be made from silicon oxide or metal, or from a mixed material of silicon oxide and silicon nitride.

The vibration system of the present invention is very small, and therefore can also be used for especially small liquid quantities or gas quantities. Known methods of semi-conductor production are used exclusively for manufacture, so that the sensors can be manufactured cost-effectively in large lots. In the process, evaluation circuits in particular can be integrated as well. Moreover, density and viscosity of a medium can be measured simultaneously by the sensor of the present invention. Piezoelectric resonator 13 is completely separated from the medium, so that materials can also be used which are attacked by the media to be measured. The materials directly in contact with the measurable medium are chemically very resistant. Because of the use of only one material for bending reed 1, hardly any thermal strains occur. Moreover, bending reed 1 is very light, so that accelerative forces as occur in a mechanically problematic environment such as a motor vehicle have only a slight influence on the vibration of bending reed 1. Piezoresistive resistor elements 3 utilized are very small, and therefore have a negligible effect of their own on bending reed 1.

Figure 3:
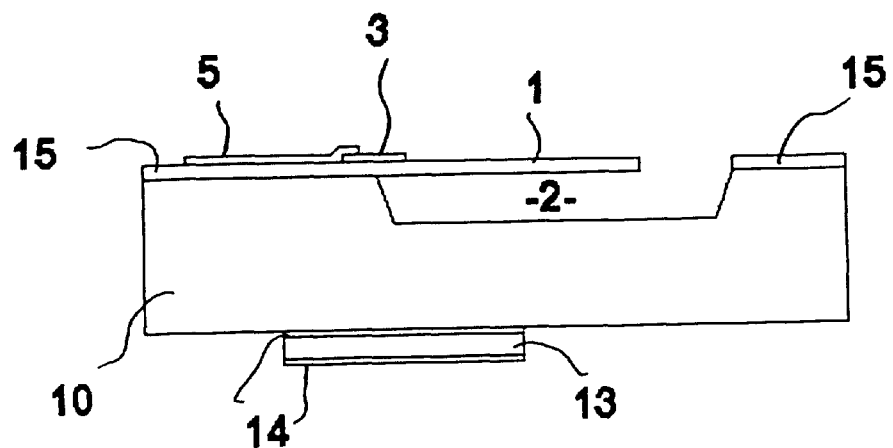
FIG. 3 shows a cross-section of a second exemplary embodiment according to the present invention.

FIG. 3 shows a cross-section of another exemplary embodiment of the sensor according to the present invention. Applied again on a substrate 10 is a silicon-nitride layer 15, out of which is structured a bending reed 1. Configured below bending reed 1 is again a groove well 2 which, however, extends to a lesser depth into substrate 10 compared to groove well 2 according to FIG. 1. Arranged again in the holding region of bending reed 1 is a piezoresistive resistor element 3 which here, however, is situated on the top side of bending reed 1. In particular, it is a piezoresistive resistor element made of polycrystalline silicon which was produced by an appropriate deposition and structuring process on silicon-nitride layer 15. Piezoresistive resistor element 3 is directly provided here with a contacting 5 which is formed, for example, by a metal layer. The top surface of piezoelectric element 3 is also provided with a thin passivation layer, not shown here, made of silicon oxide or silicon nitride, which includes contact openings for contacting 5, and otherwise protects the piezoelectric element against aggressive media. Contacting 5 here forms both a lead and a possibility for the connection of external connecting wires. A plurality of elements can again also be interconnected to form a bridge. A piezoelectric resonator 13 having metallizations 14 is again arranged on the bottom side of substrate 10. Because of the greater thickness of remaining substrate 10 under groove well 2, the vibrational energy of piezoelectric resonator 13 here is predominantly transferred by solid-matter vibrations through substrate 10. The portion of transfer through the measurable medium is small here. In this connection, it is an alternative form of excitation, in which the measurable medium itself is not needed for the energy transfer between piezoelectric resonator 13 and bending reed 1.

What is claimed is:

1. A sensor for measuring a viscosity and a density of a measurable medium, comprising:

a vibration generator;

a bending reed mechanically coupled to the vibration generator and capable of being set to a vibration in the measurable medium by the vibration generator, the measurable medium being examined by evaluating the vibration of the bending reed; and a substrate having a depression, wherein:

the bending reed is arranged on a first side of the substrate above the depression, and the vibration generator is arranged on a second side of the substrate.

2. The sensor according to claim 1, wherein the bending reed is formed from one of silicon nitride, silicon oxide, a metal, and a mixed material formed from silicon nitride, silicon oxide, and the metal.

3. The sensor according to claim 1, further comprising:
a piezoresistive element for measuring a deflection of the bending reed.

4. The sensor according to claim 3, wherein the piezoresistive element is formed as a thin-film element arranged on a top side of the bending reed.

5. The sensor according to claim 3, wherein the piezoresistive element is formed from monocrystalline silicon and is arranged on a bottom side of the bending reed.

6. The sensor according to claim 1, further comprising:
a temperature-measuring element arranged on the substrate and for measuring a temperature of the measurable medium.

7. The sensor according to claim 1, further comprising:
an integrated signal-processing circuit coupled to the substrate, wherein the substrate is formed from silicon.

8. The sensor according to claim 1, further comprising:
a device for exciting the bending reed to a vibration having one of a speed resonance frequency and an amplitude resonance frequency.

* * * * *